US006716611B2

(12) United States Patent
Dana et al.

(10) Patent No.: US 6,716,611 B2
(45) Date of Patent: Apr. 6, 2004

(54) METHOD FOR TRANSFORMING CARIOGENIC FOOD SUGARS INTO ACARIOGENIC OR CARIOSTATIC NEUTRAL PRODUCTS AND COMPOSITION THEREFOR

(76) Inventors: Jean Dominique Dana, 1609, Chemin St. Bernard, Vallauris (FR), F-06220; Nathalie Garelli-Milius, 24, Boulevard Joseph Garnier, Nice (FR), F-06000

( * ) Notice: Subject to any disclaimer, the term of this patent is extended or adjusted under 35 U.S.C. 154(b) by 59 days.

(21) Appl. No.: 10/169,335

(22) PCT Filed: Dec. 19, 2000

(86) PCT No.: PCT/FR00/03591

§ 371 (c)(1),
(2), (4) Date: Jul. 1, 2002

(87) PCT Pub. No.: WO01/49241

PCT Pub. Date: Jul. 12, 2001

(65) Prior Publication Data

US 2003/0012745 A1 Jan. 16, 2003

(30) Foreign Application Priority Data

Dec. 29, 1999 (FR) .............................................. 99 16698

(51) Int. Cl.[7] .......................... C12N 9/00; A61K 38/54
(52) U.S. Cl. ...................................... 435/183; 424/94.2
(58) Field of Search .......................... 435/183; 424/94.2

(56) References Cited

U.S. PATENT DOCUMENTS 4,150,113 A    4/1979   Hoogendoorn et al.

FOREIGN PATENT DOCUMENTS

| EP | 277383 | * | 8/1988 |
| EP | 0 277 383 | | 8/1988 |
| EP | 451972 | * | 10/1991 |
| EP | 0 451 972 | | 10/1991 |
| FR | 2 651 433 | | 3/1991 |
| FR | 2651433 | * | 3/1991 |
| WO | 88/02600 | | 4/1988 |
| WO | WO 8802600 | * | 4/1988 |

* cited by examiner

Primary Examiner—Michael Meller
(74) Attorney, Agent, or Firm—Young & Thompson

(57) ABSTRACT

A method for transforming food sugars, which acts in two ways: directly and indirectly. The method is characterised in that the main direct action consists in inhibiting glycolysis by transforming the cariogenic polyoses into non-cariogenic polyols (for example, sorbitol); the indirect action consists in the use of products derived from the polyose degradation as substrates by the inventive enzymatic system so as to reinforce prevention of plaque formation, through five mechanisms: stimulating saliva flux with the polyols; reinforcing the saliva antibacterial power by activating the physiological lactoperoxidase/by-pothiocyanate system with hydrogen peroxide; decreasing the number and pathogenicity of the bacterial environment stabilizing δ-lactones, which are not bacterial substrates for plaque formation; remineralizing the enamel by stabilizing the calcium phosphate solution with sorbitol. The invention is applicable to bucco-dental hygiene.

7 Claims, No Drawings

METHOD FOR TRANSFORMING CARIOGENIC FOOD SUGARS INTO ACARIOGENIC OR CARIOSTATIC NEUTRAL PRODUCTS AND COMPOSITION THEREFOR

The invention has for its object a process for transformation of food sugars into acariogenic or cariostatic neutral products and the composition for practicing said process.

The invention is applicable to bucco-dental hygiene.

This enzymatic composition can be used in the form of dentifrice, gel, paste, spray, pills, tablets, pastilles, chewing gum, solution or other form used in bucco-dental hygiene.

Dental caries is an infectious malady very widespread among humans. It is due to the presence in the buccal cavity of bacterial microorganisms, principally streptococcus mutans, which colonize the dental surfaces to form dental plaque.

The thickening of the dental plaque by bacteria is a function of the sugar content of food (principally saccharose), because the bacteria have all the enzymes of glycolysis.

Thus, analysis of the thickened plaque shows polysaccharides from the bacterial metabolism of saccharose and which form the substance of the matrix.

There can be distinguished:

Extra Cellular Polysaccharides

A. Soluble

Dextrans: polymers of glucose forming linear chains ∀-1,6 and multiple branches ∀-1,3 and often ∀-1,2.

Levans: linear polymers sometimes branched, of fructose. The osidic bond is of the type ∃-2,6 and ∃-2,4.

Glucans: homopolymers of glucose.

B. Insoluble

Mutans: polymers of glucose ∀-1,3 and sometimes ∀-1,6.

Intrabacterial Polysaccharides:

Amylopectin: linear polymers of glucose forming chains ∀-1,4 and branched at ∀-1,6.

Dental Plaque

Dental plaque begins with the formation of an acellular organic film comprised of amino acids and glycoproteins of saliva and bacterial origin. This permanent and non-pathogenic pellicule does not develop if the food is low in saccharose. On the contrary, it increases in thickness by agglutination and formation of several layers of soluble and insoluble glycoproteins because of the habit of eating food high in sugar.

Studies carried out as to bucco-dental hygiene have shown the presence of several bacterial strains whose glucidic metabolism is in large part responsible for the formation of dental plaque.

Sugary food and the bucco-pharyngal flora constituted principally by streptococcus mutans, sanquis and viscosiis, will hydrolyze extra cellular polysaccharides into fructose and glucose, monomeric elements assembled by the bacterial enzymes to form soluble chains in the first instance, and insoluble dextrans or mutans in the second instance. Glucans and levans also contribute to the formation of the matrix:

Glucose: dextrans, mutans and glucanes

Fructose: levans.

Soft plaque becomes mature by accumulation of viscous dextrans colonized by the bacteria ($10^8$ bacteria/mg).

Metabolism of Plaque

Plaque lives aerobically in a first instance, to rapidly become anaerobic in a mature condition.

The levans are used as hydrocarbon reserves by the bacteria, saccharose supplied by food diffuses through the matrix thus formed, and provides the energy substrate necessary for bacterial survival.

This glucidic metabolism of the plaque (glycolysis) leads to the formation of lactic acid under anaerobic conditions and gives rise to a lowering of the pH, which has a direct influence on cariogenic potential of the dental plaque.

Glycolysis

There is meant by glycolysis the degradation of the sugars by bacteria of the dental plaque, which phenomenon is determinant in the pathogenicity of dental caries.

From sugars, the bacteria synthesize extracellular polysaccharides (dextrans), from the intracellular glycogen to satisfy their energy need, and lactic acid. It is the lactic acid which destroys the hydroxyapatite crystals.

There is meant by antiglycolysis the inhibition of the formation of lactic acid from sugars introduced into the buccal cavity.

The Defense Mechanisms

The buccal tissues are continuously subjected to bacterial invasion from food. It is a warm and moist environment which seems optimal to ensure the growth of germs.

However, various defense mechanisms are used to preserve the integrity of the structures.

Salivary enzymatic components assist in protecting the solid structures against bacteria.

The lactoperoxidase system, in particular, produces hypothiocyanate which has a bactericidal role. Its limiting factor is the hydrogen peroxide which is often supplied in a very weak manner to the physiological condition in the buccal cavity.

The energy factor is extremely important to bacterial growth. Glycolysis permits the survival and development of the bacteria.

The state of the art can also be defined by the following patents:

FR 2.48.346: dentifrice composition in solid form, for human and animal use, characterized in that it comprises:
  at least one compound having antiseptic and/or anti-microbial activity,
  at least one component exerting an abrasive action,
  at least one component exhibiting an anti-tartar function,
  at least one component having the property of attacking dental plaque, and having if desired anti-microbial properties,
  and at least one compound constituting a source of fluoride.

FR 2.51.433: Enzymatic complex adapted to be associated with a support, an excipient and/or a vehicle, for its use as a dentifrice product, characterized in that with a view to providing an action of simultaneously eliminating and/or retarding the formation of dental plaque, tartar and caries, it contains at least one enzyme acting on the recent "soft" plaque, and at least one enzyme acting on the old insoluble plaque, associated with group of other enzymes whose chain of actions leads to the formation of a strongly bactericidal medium. The enzymes whose chain of actions leads to the formation of a strongly bactericidal medium is amyloglycosidase, in an amount of about 0.8%, the glucose-oxidase in an amount about 0.2% and the lactoperoxidase in an amount about 0.02%.

EP 0 414 980: Liquid dentifrice composition characterized in that it contains as essential ingredients:
  at least one antiseptic and/or anti-microbial agent,
    at least one component acting on impurities, namely tartar, and
  at least one component constituting a source of fluoride, as well as the usual additives, namely, preferably a coloring agent, a perfume, an astringent and/or a brilliance agent—the whole being in aqueous solution, provided in a receptacle having projection means for a spray jet, either by a mechanical system with pumping and cooling, or by a compressed propellant gas.

WO 93 10752: Stabilized aqueous dentifrice composition capable of producing or in the presence of saliva conducting the reduction of effective anti-microbial concentrations of hypothiocyanite ions. The composition contains both an oxodoreductase enzyme and its specific substrate, so as to produce hydrogen peroxide of at least the minimum effective concentration. The aqueous dentifrice compositions of the invention can be stabilized against enzyme/substrate interaction brought on prematurely by adjustment of the level of oxygen dissolved in the excipient of the aqueous dentifrice. It is also possible to add a peroxidase enzyme so as to act on the mentioned hydrogen peroxide, thereby oxidizing the thiocyanate ions to produce antimicrobial concentrations of hypothioxynate ions. There can be also added as desired thiocyanate ions to the composition of the invention in a dose sufficient, with the other ingredients of said invention, to produce more than about 100 micromoles/liter/minute of hypothiocyanite ions during use. The quantity of water contained in the dentifrice compositions is not important to the stability of the composition, on condition of controlling the oxygen level. The invention also relates to the process for production of the dentifrice composition with minimum oxygen content.

WO 96 0865: The invention relates to recombined layers of streptococcus mutans, which is characterized by a deficiency in production of lactic acid, as well as the preparation of a recombined alcohol dehydrogenase. These strains of streptococcus mutans are used in a method for preventive treatment of dental caries.

The process according to the invention acts as a prevent agent of the formation of dental plaque.

The process according to the invention acts in two ways: direct and indirect.

1) The principal direct action consists in inhibiting glycolysis while transforming the cariogenic polyoses in non-cariogenic polyols. This inhibition takes place in situ in the buccal cavity and permits stabilizing the pH therein above 6, thus avoiding the demineralization of the dental enamel—a principal factor responsible for dental caries.

2) The indirect action consists in the use of the products from the degradation of polyoses as substrates by the enzymatic system described in the invention, so as to reinforce the prevention of the formation of dental plaque, by five mechanisms.

2.1 Stimulation of saliva flow by polyols, 2.2 Reinforcement of the anti-bacterial power of the saliva by activation of the physiologic system LPO/Hypothiocyanate by hydrogen peroxide, 2.3 Decrease in the number and pathogenicity of the bacterial medium (streptococcus mutans) by creation of an etiological environment that is selective against it, by the polyols, 2.4 Stability of the δ-lactones, which are not bacterial substrates for the formation of dental plaque, 2.5 Remineralization of the enamel by the stabilization of the calcium phosphate solution by the sorbitol.

This synergy of actions acts for the benefit of the new composition for bucco-dental hygiene.

The process according to the invention consists in transforming overall the totality of the food sugars (glucoses, fructoses) by saccharase (invertase), then acting by a combination of enzymes contained in the composition for buccodental hygiene, on the D-glucoses and the D-fructoses, said enzymatic complex permitting obtaining for:

1-glucose dehydrogenase→D-glucono-*-lactone, 2-glucose oxidase→D-gluconic acid+$H_2O_2$ (hydrogen peroxide), 3-sorbitol dehydrogenase→D sorbitol.

Thus, the process acts simultaneously on the food sugars, on the dental plaque by transforming the fructose polymers into sorbitol, on the dental plaque by transforming the glucose polymers (activation of the saliva physiologic defense).

The composition for practicing the process is essentially characterized by the combination of an enzymatic complex such as:

an enzyme or mixture of enzymes hydrolyzing the bonds Ǝ-2,6 and/or Ǝ-2,1 between fructofuranosyles (for example sacchrase (invertase)), an oxydo-reductase permitting the transformation of the glucose (glucose oxidase and/or glucodehydrogenase), an oxydo-reductase permitting the transformation of fructose into sorbitol.

According to a preferred embodiment, the oxydo-reductase is a sorbitol dehydrogenase enzyme.

According to another embodiment, the enzymatic complex of the composition is comprised by the following enzymes:

invertase, glucose-oxidase and/or glucose dehydrogenase, amyloglucosidase, sorbitol dehydrogenase.

The composition in liquid form, solid (pastes, tablets, chewing gum, pills), mouthwash or spray for practicing the process is the following:

| | |
|---|---|
| Enzymatic system | 1.5% |
| Invertase | |
| Glucose oxidase and/or glucose dehydrogenase | |
| Amyloglucosidase | |
| Sorbitol dehydrogenase | |
| Aminated fluorine (cetylamine hydrofluoride) | 0.005% |
| and/or Sodium Fluoride | 0.01% |
| Dimethicone | 1.5% |
| Polysorbate 80 | 1.4% |
| Polysorbate 20 | 1.4% |
| Sodium Saccharinate | 0.15% |
| Glycerol | 10% |
| Sorbitol | 40% |
| Xylitol | 5% |
| Colloidal Silica | 1% |
| Perfume | 1% |
| Preservative | 0.15% |
| Water | QSP 100% |

The composition in the form of solid dentifrice (paste, pills, chewing gum, tablets), of semi-liquid gel or in liquid form in water bath is the following:

| | |
|---|---|
| Enzymatic System | 1.5% |
| Invertase | |
| Glucose oxidase | |
| Amyloglucosidase | |
| Sorbitol | 50% |
| Zinc Citrate | 0.2% |

-continued

|  |  |
|---|---|
| Calcium Bicarbonate | 0.1% |
| Xylitol | 15% |
| Fluoride | <0.1 |
| Dimethicone | 0.5% |
| Colloidal silica | 1% |
| Preservative/antiseptic | 0.5% |
| Sodium Saccharinate | 0.2% |
| Mint flavoring | 1% |
| Water | QSP 100% |

The composition in the form of a dentifrice of semi-liquid gel or in spray form is the following:

|  |  |
|---|---|
| Enzymatic system | 1.5% |
| Invertase |  |
| Glucose oxidase |  |
| Amyloglucosidase |  |
| Sorbitol dehydrogenase |  |
| Zinc Citrate | 0.2% |
| Calcium Bicarbonate | 0.1% |
| Xylitol | 15% |
| Sorbitol | 50% |
| Dimethicone | 0.5% |
| Colloidal silica | 1% |
| Preservative/antiseptic | 0.5% |
| Sodium Saccharinate | 0.2% |
| Mint flavoring | 1% |
| Water | QSP 100% |

According to another embodiment, the enzymatic complex is comprised of the following enzymes:

Invertase

Glucose-oxidase and/or glucose dehydrogenase

With or without amyloglucosidase
    And associated with sorbitol whose concentration in the final composition is equal to or greater than 15%
    And/or associated with xylitol whose concentration in the final composition is equal to or greater than 10%
    Or associated with a mixture of sorbitol and xylitol whose concentration in the final composition is equal to or greater than 20%

The percentages and quantities of enzyme U/g described are given by way of example and are not limiting in the claims.

Numerous studies have shown that the replacement of rapid sugars (saccharose) by polyols (sorbitol—xylitol) had a direct effect (up to more than 80%) on the decrease of caries. (International Symposium—January 1988).

Mechanism

Streptoccocus mutans is one of the most acid bacteria, which cannot survive without available saccharose or glucose.

The polyols are not fermented in two acids by streptococcus mutans, and enter into competition with the polyoses to take part in the metabolism of the bacteria. One of the theories is that the polyol is phosphorylated by streptococcus mutans when it is transported by the cell—or accumulates—and in which the polyol-5-phosphate interrupts the normal metabolism of the bacterial cell and can alter its external envelope.

The bacteria survive in the buccal cavity, because they can tolerate modifications in the conditions of their environment.

The polyols render the bacteria more sensitive to their environment unless adapted to become dominant in the dental plaque or the carious sites. There is noted a reaction of the plaque in experiments in which the polyols replace or are in competition with the polyoses, as well as a significant reduction of the number of streptococcus mutans. On the other hand, the polyols stimulate the secretion of saliva, decreasing the acid content, taking part with Ca++, by formation of complexes, in direct effects on the remineralization of the enamel.

In short, the polyols are non-cariogenic sugars having a potential of cariostatic properties.

The replacement or transformation in the mouth, of saccharose, into polyols (sorbitol) seems to affect more than one process normally necessary to the development of cariogenic lesions.

Until now, only the substitution of sugar with polyols existed (chewing gum, dietetics).

Thanks to the process of the invention described hereafter, the transformation of cariogenic sugar in food into non-cariogenic polyols, will take place specifically in the dental plaque and in the buccal cavity, to decrease significantly glycolysis.

The Antibacterials

The antibacterials (chlorexidine, hexomedine, trichlosan, triclarban . . . ) have been the principal products used to counter dental plaque and caries, as antiseptic agents to combat the proliferation of bacteria. They have a major drawback: their systematic use gives rise to bacterial mutations with the appearance of polyresistant microbes.

The Enzymes

Different types of enzymes have been proposed and can be grouped into three large categories.

Antibacterial Enzyme System

Several patents have described antibacterial systems by reinforcing the saliva lactoperoxidase.

Laclede Patent No. EP 0 133 736 thus augments the saliva by supplying exogenous lactoperoxidase, glucose oxidase and potassium thiocyanate.

The principal drawback is the need to add glucose in the composition which is a substrate for bacterial metabolism.

Antiplaque Enzyme System Acting Directly on the Dental Plaque

Several patents describe enzymatic systems which act directly on the polymers constituting dental plaque, namely the dextrans, the mutans and the glucans.

French patent 2.502.958 discloses a combination mutanase and dextranase which acts by specific hydrolysis on the polyglucosidic bonds of the mutans (insoluble) and the dextrans (soluble).

The patent FR-A-89 11868 also provides enzymatic hydrolysis of the mutans and dextrans, but reinforces and extends this action by conjoint use of amyloglucosidase which acts specifically on amylopectin.

It uses the glucose obtained by these different hydrolyses, to form hydrogen peroxide used by the lactoperoxidase of the exogenous complex, and gives off free radical oxygen capable of oxidizing the thiocyanates and hypothiocyanates (LP system), which are the powerful bactericides adapted to intervene in streptococcus mutans.

As to the fructose polymers of the dental plaque, nothing is described in the prior art.

Antiglycolysis Enzyme Systems

Few Patents Relate to the Complete Blockage of Bacterial Glycolysis

Certain act directly by having an antibacterial action.

Others act by countering the consequences of this glycolysis on the modification of pH.

No present enzymatic system acts overall and none transforms totally cariogenic sugar derivatives into neutral or acariogenic substances.

This is the object of the present invention.

DESCRIPTION OF THE INVENTION

The present invention relates to a group of enzymes that can be used to inhibit glycolysis in the bucco-dental region, and as agents for direct or indirect prevention of the formation of dental plaque.

Until now, all the enzymes used in this field acted only on the glucose or glucose polymers (mutans, dextrans, amylopectin . . . ) which they hydrolyzed to generate glucose units.

Only French patent 89 11868 transforms these glucose units to form bactericidal hypothiocyanate, thanks to the LP system.

The enzymatic complex of the present invention permits inhibiting glycolysis by transforming cariogenic sugars into acariogenic or neutral elements, and indirectly reinforces the prevention of the formation of dental plaque.

This new enzymatic composition acts on:

The food saccharose to give glucose and fructose
1. The levans of the plaque to give fructose units
2. The fructose units obtained either by degradation of the levans, or by hydrolysis of the saccharose to give acariogenic products
3. The glucose units obtained either by degradation of the dental plaque (dextrans, mutans, glucans, amylopectin), or by hydrolysis of the saccharose to give inert products.

The transformation of the food saccharose into fructose and glucose units is carried out by an invertase such as saccharase for example.

The degradation of the polymers of fructose of the levans into fructose units can be carried out by a mixture of enzymes hydrolyzing the bonds β-2,6 and/or β-2,1 between fructofuranosyles.

The fructose units obtained by inversion of the food saccharose, and/or hydrolysis of the levans, are used as substrates by an oxydo-reductase such as sorbitol dehydrogenase (EC 1.1.1.14) for example—which reduces these fructose or polyol units, namely the sorbitol. In this case, the enzymatic degradation of the dental plaque (levans in particular) permits obtaining sorbitol whose acariogenic property is known to those skilled in the art.

The glucose units obtained, either by inversion of the food saccharose, or by enzymatic hydrolysis of the polyglucosids constituting the dental plaque, can be used as a substrate by an oxydo-reductase-glucose dehydrogenase for example—to be reduced to neutral D-glucono-*-lacone and/or used as substrates by a glucose-oxidase to give glucuronic acid and hydrogen peroxide. This latter becomes the factor facilitating the saliva lactoperoxidase system, and contributes to obtaining physiological and anti-bacterial hypothiocyanate.

What is claimed is:

1. A composition for improving bucco-dental hygiene, comprising:
    a) invertase;
    b) at least one of glucose-oxidase and glucose dehydrogenase; and
    c) sorbitol dehydrogenase.

2. The composition according to claim 1, further comprising amyloglucosidase.

3. The composition according to claim 1, further comprising:
    sorbitol;
    xylitol; or
    a mixture of sorbitol and xylitol.

4. The composition according to claim 2, further comprising:
    sorbitol;
    xylitol; or
    a mixture of sorbitol and xylitol.

5. The composition according to claim 1, wherein the composition is in liquid form and comprises:
    1.5% of an enzymatic system containing a) invertase, b) at least one of glucose oxidase and glucose dehydrogenase, c) amyloglucosidase, and d) sorbitol dehydrogenase;
    0.005% of aminated fluorine;
    0.01% of sodium fluoride;
    1.5% of dimethicone;
    1.4% of polysorbate 80;
    1.4% of polysorbate 20;
    0.15% of sodium saccharinate;
    10% of glycerol;
    40% of sorbitol;
    5% of xylitol;
    1% of colloidal silica;
    1% of perfume;
    0.15% of preservative; and
    QSP 100% of water.

6. The composition according to claim 1, wherein the composition is in the form of a dentifrice or a spray, and comprises 1.5% of an enzymatic system containing a) invertase, b) glucose oxidase, c) amyloglucosidase, and d) sorbitol dehydrogenase;
    0.2% of zinc citrate;
    0.1% of calcium bicarbonate;
    15% of xylitol;
    50% of sorbitol;
    0.5% of dimethicone;
    1% of colloidial silica;
    0.5% of a preservative or antiseptic;
    0.2% of sodium saccharinate;
    1% of mint flavoring; and
    QSP 100% of water.

7. The composition according to claim 1, wherein the composition comprises the following: 1.5% of an enzymatic system containing a) invertase, b) glucose oxidase, c) amyloglucosidase, and d) sorbitol;
    0.2% of zinc citrate;
    0.1% of calcium bicarbonate;
    15% of xylitol;
    <0.1% of fluoride;
    0.5% of dimethicone;
    1% of colloidal silica;
    0.5% of a preservative or antiseptic;
    0.2% of sodium saccharinate;
    1% of mint flavoring; and
    QSP 100% of water.

* * * * *